United States Patent
Blades et al.

[19]

[11] Patent Number: 6,047,712
[45] Date of Patent: Apr. 11, 2000

[54] FLOSS DISPENSER

[75] Inventors: Helena C. Blades, Toledo; Bradley J. Kimble, Holland, both of Ohio

[73] Assignee: Owens-Illinois Closure Inc., Toledo, Ohio

[21] Appl. No.: 09/250,228

[22] Filed: Feb. 13, 1999

[51] Int. Cl.[7] .............................. A61C 15/00; A45D 44/18
[52] U.S. Cl. ........................ 132/325; 132/324; 132/323; 132/309
[58] Field of Search ..................................... 132/325, 324, 132/309, 323, 321, 327, 328, 329, 322; 206/63.5, 368

[56] References Cited

U.S. PATENT DOCUMENTS

| | | | |
|---|---|---|---|
| 2,893,405 | 7/1959 | Castelli | 132/325 |
| 4,026,063 | 5/1977 | Allen et al. | 206/408 |
| 4,428,389 | 1/1984 | Sánchez Cordero | 132/325 |
| 4,673,106 | 6/1987 | Fishman | 222/80 |
| 4,796,783 | 1/1989 | Paulson | 222/80 |
| 4,827,951 | 5/1989 | Grussmark | 132/314 |
| 4,934,389 | 6/1990 | Pettiford | 132/325 |
| 5,335,827 | 8/1994 | Gentile | 222/137 |
| 5,415,187 | 5/1995 | Heneveld | 132/325 |
| 5,449,092 | 9/1995 | Bazan | 222/93 |
| 5,544,754 | 8/1996 | Stahl | 206/581 |
| 5,638,840 | 6/1997 | Lee et al. | 132/310 |
| 5,645,193 | 7/1997 | Gentile et al. | 222/137 |
| 5,732,722 | 5/1998 | Mortvedt | 132/325 |

*Primary Examiner*—John J. Wilson
*Assistant Examiner*—Robyn K Doan

[57] ABSTRACT

A dental floss dispenser is disclosed, which is adapted for mounting onto a pump toothpaste dispenser. The dental floss dispenser has a one-piece housing of integrally molded plastic construction which has a peripheral contour to match the predetermined bottom configuration of the toothpaste dispenser. The housing has a base with a peripheral wall having a recessed ledge and slot in the peripheral wall to dispense the floss. The dental floss spool is rotatably mounted on one of two bosses in the housing. The housing also has a hinged door which matches the predetermined bottom configuration of the toothpaste dispenser which is capable of movement away and against the peripheral base wall to expose the slot through which the floss is dispensed. A cutter is mounted on the hinged door allowing the severing of a desired length of floss pulled from the spool through the slot. The hinged door may be kept in a closed position when not in use to prevent external contamination between use of the dental floss or cutter.

9 Claims, 2 Drawing Sheets

FLOSS DISPENSER

TECHNICAL FIELD

The present invention relates to an integrally molded dispenser for dental floss which is adapted to be attached to the base of a toothpaste dispenser. Dental floss is primarily utilized by consumers for the cleaning of food particles lodged between the teeth. This invention relates to a dental floss dispenser which is capable of becoming an integral part of a pump type toothpaste dispenser.

BACKGROUND OF THE INVENTION

Dental floss dispensers having a housing, a cap, a dispensing aperture and a blade for severing the floss are known to the art. Toothpaste dispensers, such as the pump type toothpaste dispensers are also known to the art. Numerous dispensers such as shown in U.S. Pat. No. 4,934,389 have also been made which combine both the toothpaste dispenser and the floss dispenser eliminating the need to carry both dispensers separately, and saving space.

Prior art discloses a combination of toothbrush and dental floss dispenser, wherein dental floss is stored and dispensed from the handle of a toothbrush such as disclosed in U.S. Pat. No. 5,415,187. Prior art also discloses a combination toothpaste dispenser and floss dispenser, wherein the dental floss dispenser is either mounted on the top of the toothpaste dispenser in the cap or inserted in the base of the toothpaste dispenser as disclosed in U.S. Pat. Nos. 4,827,951 and 4,673,106.

SUMMARY OF THE INVENTION

The dental floss dispenser disclosed herein is adapted to be attached to the base of a toothpaste dispenser and may be used in combination with the toothpaste dispenser or may be used separately in accordance with the preference of the user. The dental floss dispenser in the present invention is made of a one-piece plastic housing having a peripheral contour to match the predetermined bottom configuration of a toothpaste dispenser eliminating multiple manufacturing steps and decreasing manufacturing costs. The dental floss dispenser disclosed herein is adapted to be attached to the toothpaste dispenser. Prior art discloses dental floss dispensers which are inserted into the cavity of a toothpaste dispenser. The advantage of the present invention is that the dental floss dispenser may be peripherally contoured to match and attach to multiple toothpaste dispensers and thus providing an easy mechanism for attachment. The dental floss dispenser disclosed herein also provides easy access to the dental floss either when attached to a toothpaste dispenser or used separately through a hinged door which may be open and shut to access the dental floss.

An embodiment of the dental floss dispenser of this invention comprises a one-piece plastic housing having bosses which may receive a dental floss spool, a peripheral wall surrounding the bosses having a slot to expose a length of floss to be used and a recessed ledge to allow fitment on to toothpaste dispenser. The peripheral base wall has a hinged door capable of opening and closing to expose the slot and to house a cutter. The hinged door is also peripherally contoured to match the predetermined bottom configuration of the toothpaste dispenser. The dental floss dispenser is adapted to be attached to the toothpaste dispenser either by the recessed ledge above the peripheral base wall surrounding the housing or the bosses within the housing or both. The dispenser can also be adapted to allow the storing of an extra dental floss spool with the dental floss dispenser.

Once a suitable length of the dental floss is pulled through the slot in the peripheral base wall by the user, the dental floss drawn may be severed by the cutter mounted on the door by sliding the dental floss underneath the raised cutter and pulled against the cutter to cut the desired length of the dental floss. Should the user desire, he or she may also store an extra dental floss spool which may also be pulled and severed in a similar manner as described above. The cutter mounted on the hinged door is also easily replaceable without replacing the entire dental floss dispenser should it become dull from repeated use.

The above-mentioned features and objects of this invention and the manner of attaining them will become more apparent and the invention itself will be understood by reference to the following description of an embodiment of the invention, when considered in conjunction with the accompanying drawings.

DETAILED DESCRIPTION

Figure 1:
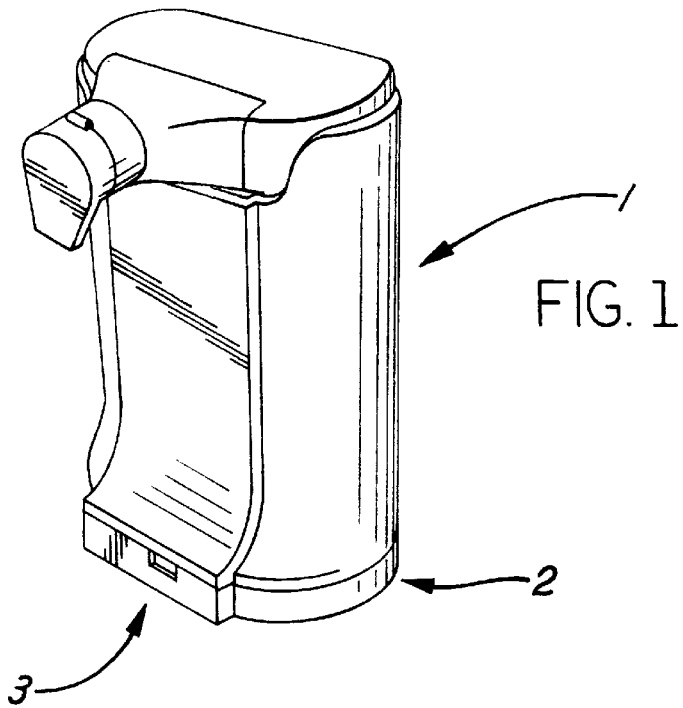
FIG. 1 is a perspective view of the floss dispenser in combination with Mentadent toothpaste dispenser such as the one shown in U.S. Pat. No. 5,335,827.

FIG. 1 shows the toothpaste dispenser 1, and attached thereto a dental floss dispenser 2, having a hinged door 3. The FIG. shows the dental floss dispenser attached to the base of the toothpaste dispenser where the dental floss dispenser is peripherally contoured to match the predetermined bottom configuration of the toothpaste dispenser.

Figure 2:
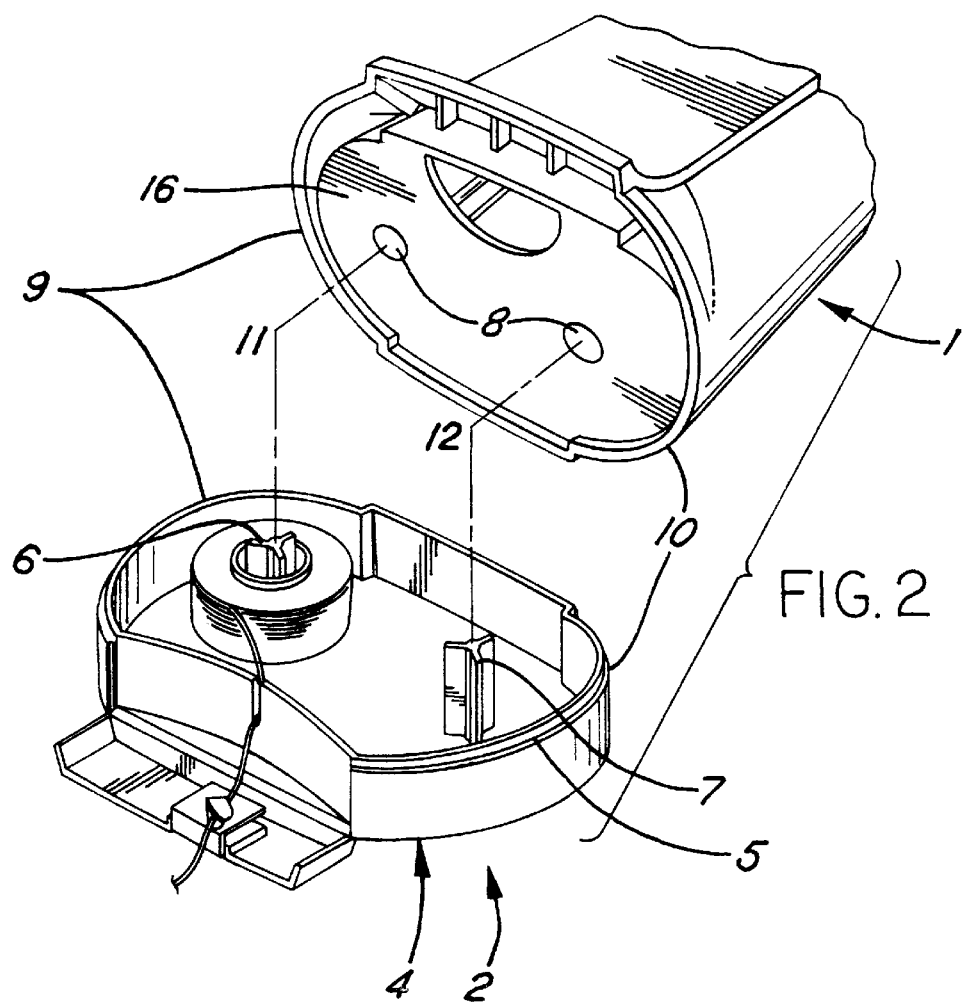
FIG. 2 is a fragmentary exploded perspective view to show how the floss dispenser may be attached to the toothpaste dispenser.
Figure 4:
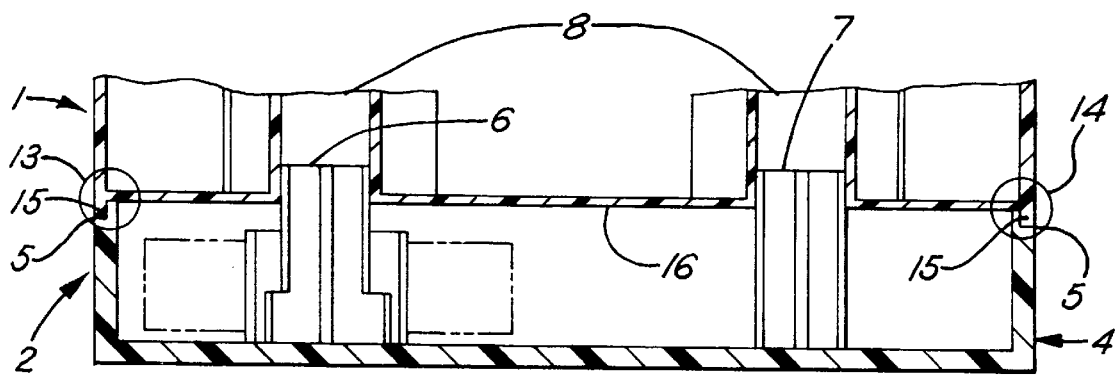
FIG. 4 is a fragmentary sectional view that shows the floss dispenser assembly assembled to the toothpaste dispenser.

FIG. 2 is a fragmentary exploded perspective view showing the attachment means of the floss dispenser 2 to toothpaste dispenser 1. The floss dispenser 2 is attached to toothpaste dispenser 1 by the recessed ledge 5 which is circumferentially above the peripheral base wall 4 is designed so that it may snap fit within the bottom perimeter of the toothpaste dispenser as generally depicted by arrows 9 and 10. FIG. 4 is a fragmentary sectional view of the bottom of FIG. 2 that shows the floss dispensing assembly 2 attached to the toothpaste dispenser. The bottom perimeter of the toothpaste dispenser would fit around the recessed ledge of the floss dispenser 2. The attachment is also shown in FIG. 4 at locations 13 and 14. As shown in FIG. 4, the dental floss dispenser is attached to the toothpaste dispenser 1 so that the bottom of the toothpaste dispenser 15, contoured below the base of the toothpaste dispenser 16, is fitted with the recessed ledge 5 generally depicted within locations 13 and 14, and attached circumferentially around the toothpaste dispenser.

The preferred embodiment in FIG. 2 also shows another mechanism for attaching the floss dispenser to the toothpaste dispenser. Floss dispenser 2 may also be attached to the toothpaste dispenser 1 wherein the bosses 6 and 7 housed within the toothpaste dispenser, either of which adapted to rotatably receive a dental floss spool, may be attached by friction fit into the orifices 8 in the bottom of the toothpaste dispenser as generally depicted by arrows 11 and 12.

Figure 3:
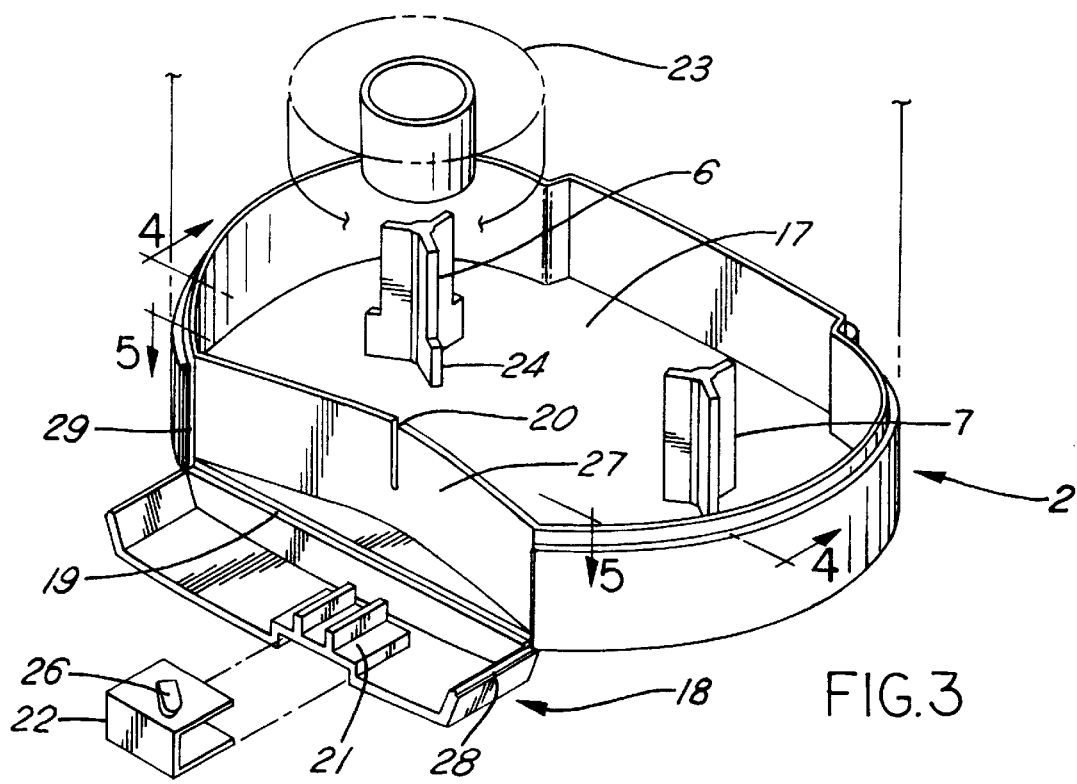
FIG. 3 is an exploded perspective view of the floss dispenser assembly.

FIG. 3 is an exploded perspective view of the floss dispenser 2. This figure shows a one-piece plastic construction housing 17 having a peripheral base wall 4 around the circumference of the housing. The peripheral base wall is indented at 27 in a V-shape at the front section of the floss dispenser having a slot 20 to guide the dental floss. A door 18 positioned below the indented peripheral base wall has a peripheral contour to match the bottom contour of the toothpaste dispenser and has a hinge 19 to allow the door to be capable of movement against and away from said indented peripheral base wall to expose the dental floss 25 extended through slot 20 for use by consumer. The door 18 in FIG. 3 includes a plastic bridge-like step 21 which is adapted to receive cutter 22. The housing 17 in FIG. 3 also includes two bosses 6 and 7 which are adapted to receive the dental floss spool 23. One of two bosses 6 has a wider base 24 allowing a snug fit of the dental floss spool 23 so that the spool is rotatably secured onto the boss.

Figure 5:
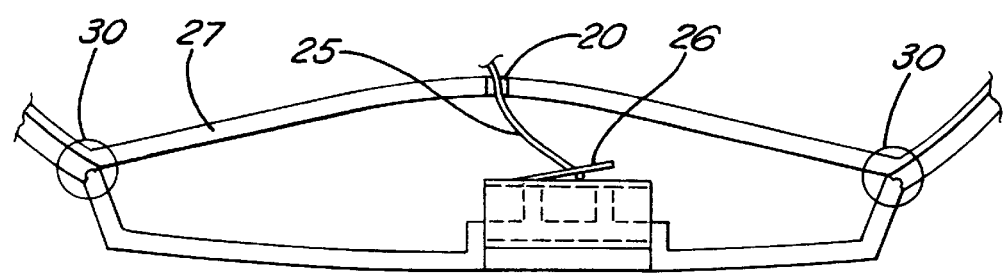
FIG. 5 is a fragmentary top plan view of the floss dispenser door and cutter.

FIG. 5 is a fragmentary cross sectional top plan view of the floss dispenser door 18 and cutter 22. Once the dental floss spool 23 is fitted over one of said bosses 6 or 7, the floss 25 may be pulled through the slot 20 as shown in FIG. 5 and positioned below the cutter knife element 26 so that it may be severed by user once a desired length of the floss is pulled through the slot 20.

Once the floss dispenser containing the floss spool is attached to the toothpaste dispenser, to expose the dental floss for subsequent use, user pulls door 18 away from the indented peripheral base wall 27 exposing slot 20 so that the desired amount of dental floss 25 may be pulled through said slot 20. Once a desired amount of dental floss is pulled through said slot, user may sever the dental floss by positioning said floss below the cutter knife element 26 and biased against said cutter knife element to cut the dental floss as shown in FIGS. 2 and 5. The hinged door 18 may then be pushed toward the indented base wall 27 to protect the exposed floss within slot 20 for storage until subsequent use. As shown in FIG. 3, the recessed portion of the door has snap beads 28 which frictionally fit with horizontal recesses 29 on the peripheral base wall in the closed position. The fit is also generally depicted in FIG. 5 at location 30.

Although the invention has been illustrated and disclosed with reference to a specific embodiment, it is to be understood that modifications may be made to the invention without departing from the spirit of the invention or from the scope of the following claims.

We claim:

1. A floss dispenser adapted to be mounted on a toothpaste dispenser of predetermined bottom configuration, said floss dispenser comprising:
   (a) a one-piece housing of molded plastic construction having a peripheral contour to match the predetermined bottom configuration of the toothpaste dispenser;
   (b) said housing having a base with a peripheral base wall and a slot in the peripheral base wall;
   (c) said base with peripheral base wall having a door hinged to said base, said hinged door having a peripheral contour to match the predetermined bottom configuration of the toothpaste dispenser;
   (d) said door hinged to said base for rotational movement for covering and exposing said slot;
   (e) a cutter mounted on said door;
   (f) said housing with said base having at least one boss adapted to receive a dental floss spool;
   (g) said housing having a means for attaching the housing to the bottom of the toothpaste dispenser.

2. The floss dispenser of claim 1, wherein said means for attaching the housing to the bottom of a toothpaste dispenser includes said boss extending above said peripheral base wall of the housing for frictional engagement into an orifice of the toothpaste dispenser.

3. The floss dispenser of claim 1, wherein said means for attaching the housing to the bottom of the toothpaste dispenser includes a recessed ledge on the peripheral base wall capable of attachment to the bottom contour of the toothpaste dispenser.

4. The floss dispenser of claim 1, having two bosses, one of said bosses having a larger diameter adapted to receive a dental floss spool.

5. The floss dispenser of claim 1, further comprising the spool of dental floss rotatably mounted on said boss within said housing, with the floss extending through said slot.

6. The floss dispenser of claim 1, said door having a snap bead which frictionally fits with a horizontal recess on the peripheral base wall for opening and closing said door.

7. A toothpaste dispenser in combination with a floss dispenser having a floss spool, said floss dispenser being mounted on said toothpaste dispenser and comprising a housing having a base with a peripheral base wall, a slot in said peripheral base wall and a door hinged to said base, wherein said housing and said door having a peripheral contour to match a predetermined bottom configuration of the toothpaste dispenser.

8. A method of making a floss dispenser adapted to be mounted on a toothpaste dispenser of predetermined bottom configuration, the steps of:
   (a) providing a one-piece housing of integrally molded plastic construction, said housing having a base having a peripheral wall, a slot in said peripheral wall and a door hinged to said base for movement against and away from said peripheral wall for covering and exposing said slot, said housing including said door having a peripheral contour to match the predetermined bottom configuration of the toothpaste dispenser;
   (b) providing means on the housing for affixing the housing to the bottom of a toothpaste dispenser;
   (c) rotatably mounting a spool of dental floss within said housing with the floss extending through said slot; and
   (d) providing means for severing a length of floss pulled from said spool through said slot.

9. The method set forth in claim 8 comprising the additional steps of:
   (a) providing a toothpaste dispenser having a bottom configuration of said predetermined contour; and
   (b) mounting said housing on the bottom of said toothpaste dispenser.

* * * * *